United States Patent
Beatty et al.

(10) Patent No.: US 10,941,436 B2
(45) Date of Patent: *Mar. 9, 2021

(54) METHODS FOR CHARACTERIZING DNA SEQUENCE COMPOSITION IN A GENOME

(71) Applicant: PIONEER HI-BRED INTERNATIONAL, INC., Johnston, IA (US)

(72) Inventors: Mary Beatty, Earlham, IA (US); Kevin Hayes, Urbandale, IA (US); Jenna Hoffman, Grimes, IA (US); Haining Lin, Clive, IA (US); Gina Marie Zastrow-Hayes, Urbandale, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

This patent is subject to a terminal disclaimer.

(21) Appl. No.: 16/598,341

(22) Filed: Oct. 10, 2019

(65) Prior Publication Data
US 2020/0032320 A1 Jan. 30, 2020

Related U.S. Application Data

(63) Continuation of application No. 15/711,403, filed on Sep. 21, 2017, now Pat. No. 10,487,352, which is a continuation of application No. 14/255,144, filed on Apr. 17, 2014, now Pat. No. 9,797,001.

(60) Provisional application No. 61/812,876, filed on Apr. 17, 2013, provisional application No. 61/813,001, filed on Apr. 17, 2013.

(51) Int. Cl.
| | | |
|---|---|---|
| *C12P 19/34* | (2006.01) | |
| *C12Q 1/6806* | (2018.01) | |
| *C12Q 1/6869* | (2018.01) | |
| *C12Q 1/6895* | (2018.01) | |

(52) U.S. Cl.
CPC ......... *C12Q 1/6806* (2013.01); *C12Q 1/6869* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | |
|---|---|---|
| 2003/0148313 A1 | 8/2003 | Strathmann |
| 2009/0202984 A1 | 8/2009 | Cantor |
| 2010/0028873 A1 | 2/2010 | Belouchi |
| 2010/0143908 A1 | 6/2010 | Gillevet |
| 2012/0015821 A1 | 1/2012 | Raymond |
| 2012/0034603 A1 | 2/2012 | Oliphant |
| 2012/0178635 A1 | 7/2012 | Dutta |
| 2013/0005585 A1 | 1/2013 | Anderson |
| 2013/0130920 A1 | 5/2013 | Zehui |

FOREIGN PATENT DOCUMENTS

| | | |
|---|---|---|
| WO | 2001042510 A2 | 6/2001 |
| WO | 2002101088 A2 | 12/2002 |
| WO | 2008134867 A1 | 11/2008 |
| WO | 2011156529 A2 | 12/2011 |
| WO | 2013036929 A1 | 3/2013 |
| WO | 2013192292 A1 | 12/2013 |

OTHER PUBLICATIONS

Black et al., "The Aldehyde Dehydrogenase Gene Superfamily Resource Center." Human Genomics. (2009) 4(2): 136-142.
Clancy, S. "DNA damage & repair: mechanisms for maintaining DNA integrity." Nature Education. (2008) 1(1):103.
Brisco Michael J. et al. "Incorporation of measurement of DNA integrity into qPCR assays." BioTechniques. (2010) 49(6): 893-897.
Griffin, et al.; "A next-generation sequencing method for overcoming the multiple gene copy problem in polyploid phylogenetics, applied to Poa grasses", BMC Biology (2011) BioMed Central 9:19.
Monson-Miller, et al.; "Reference genome-independent assessment of mutation density using restriction enzyme-phased sequencing", BMC Genomics (2012) BioMed Central 13:72.
Urbanski, et al.; "Genome-wide LORE1 retrotransposon mutagenesis and high-throughput insertion detection in Lotus japonicus", The Plant Journal (2012) 69, 731-741.
ISR and Written Opinion for International Application No. PCT/US2014/034476, dated Jul. 23, 2014.
Dubose, et al.; "Use of miscroarray hybrid capture and next-generation sequencing to identify the anatomy of a transgene"; Nucleic acids Research (2013) 41(6):e70; Oxford University Press; Oxford, UK.
Kovalic, et al.; "The Use of Next Generation Sequencing and Junction Sequence Analysis Bioinformatics to Achieve Molecular Characterization of Crops Imrpoved Through Moder Biotechnology"; The Plant Genome (2012) 5(3):149-163; Crop Science Society of America; Madison WI US.
Williams-Carrier, et al.; "Use of Illumina sequenceing to identify transposon insertions underlying mutant phenotypes in hig-copy Mutator lines of maize"; The Plant Journal (2010) 63:167-177; Blackwell Publishing Ltd.; Oxford, UK.
D'Argenio, et al.; "DNA Sequence Capture and Next-Generation Sequencing for the Molecular Diagnosis of Genetic Cariomyopathies"; The Journal of Molecular Diagnositics (2014) 16(1):32-44; Elsevier, Inc. Amsterdam, The Netherlands.
Wahler, et al.; "Next-Generation Sequencing as a Tool for Detailed Molecular Characterisation of Genomic Insertions and Flanking Regions in Genetically Modified Plants: a Pilot Study Using a Rice Event Unauthrised in the EU": Food Anal. Methods (2013) 6:1718-1727; Springer Science+Business Media; New York, NY US.

(Continued)

*Primary Examiner* — Kenneth R Horlick

(57) ABSTRACT

Methods for the high-throughput analysis of transgenic events are herein disclosed. The methods use libraries of sheared genomic DNA ligated to specialized adapters and pooled for sequence analysis and comparison to known genomic and insert sequence. The method finds use in detecting characterizing insertion site, transgene integrity, and transgene copy number.

25 Claims, 11 Drawing Sheets

Specification includes a Sequence Listing.

(56) References Cited

OTHER PUBLICATIONS

Yang, et al.; "Characterization of GM events by insert knowledge adapted re-sequencing approaches"; Scientific Reports (2013) 3:2839; Nature Publishing Group, London UK.
Amstutz, et al.; "Sequence Capture and Next-Generation Resequencing of Multiple Tagged Nucleic Acid Samples for Mutation Screening of Urea Cycle Disorders". Clincal Chemistry (2011) 57 (1) 102-111; Molecular Diagnostics and Genetics.
NimbleGen Seq Cap EZ Library LR Users Guide, version 2.0, p. 1-52, Nov. 2011, Roche NimbleGen, Inc, Madison, WI.
Ustek et al. A genome-wide analysis of lentivector integration sites using targeted sequence 2 capture and next generation sequencing technology, Infection, Genetics and Evolution, vol. 12, p. 1349-1354, May 14, 2012.
Baillie et al., Somatic retrotransposition alters the genetic landscape of the human brain, Nature, vol. 479, p. 534-537, Supplementary Information p. 1-18, Oct. 30, 2011.
Dubose et al., Use of microarray hybrid capture and next-generation sequencing to identify the anatomy of a transgene, Nucleic Acids Research, vol. 41 :e70, p. 1-5, Nov. 11, 2013.
Illumina TruSeq® DNA Sample Preparation Guide, p. i-138, Jul. 2012.
Teer et al., Systematic comparison of three genomic enrichment methods for massively parallel DNA sequencing, Genome Research, vol. 20, p. 1420-1431, Sep. 1, 2010.
454 Sequencing Rapid Library Preparation Method Manual, p. 1-8,May 2011,454 Life Sciences Corp., Branford, CT.
Duncavage et al., Hybrid capture and next generation sequencing identify viral integration sites from formalin-fixed paraffin-embedded tissue, Journal of Molecular Diagnostics, vol. 13, p. 325-333, May 2011.

Continued from Fig. 3A →→

| Junction Position | Proximal Source | Proximal Sequence Length (bp) | Proximal Hit Location | Proximal Percent Identity | Distal Source | Distal Sequence Length (bp) | Distal Hit Location | Distal Percent Identity |
|---|---|---|---|---|---|---|---|---|
| 18107 | CONSTRUCT | 154 | 18107-18260 | 100 | GENOME | 450 | Ch9:150700629-150701078 | 100 |
| 33833 | CONSTRUCT | 1709 | 32125-33833 | 100 | GENOME | 373 | Ch9:150701096-150701461 | 99.73 |
| 33849 | CONSTRUCT | 114 | 33736-33849 | 100 | CONSTRUCT | 3473 | 30360-33833 | 99.97 |

Continued from Fig. 4A

| Junction Position | Proximal Source | Proximal Sequence Length (bp) | Proximal Hit Location | Proximal Percent Identity | Distal Source | Distal Sequence Length (bp) | Distal Hit Location | Distal Percent Identity |
|---|---|---|---|---|---|---|---|---|
| 14759 | CONSTRUCT | 3743 | 11017-14759 | 100 | GENOME | 497 | Ch6:106760953-106761447 | 99.60 |
| 1472 | CONSTRUCT | 876 | 1472-2347 | 100 | CONSTRUCT | 70 | 1472-1541 | 100.00 |
| 14787 | CONSTRUCT | 3771 | 11017-14787 | 100 | GENOME | 370 | Ch9:83187058-83187427 | 98.92 |
| 14779 | CONSTRUCT | 3763 | 11017-14779 | 100 | GENOME | 570 | Ch9:83187452-83188021 | 98.95 |
| 1479 | CONSTRUCT | 869 | 1479-2347 | 100 | GENOME | 619 | Ch6:106760306-106760932 | 98.38 |

| Status | Construct | Pos | Unique_count | Total_count | 30_20 mer |
|---|---|---|---|---|---|
| 5p | 987A | 11708 | 69 | 3183 | AAGTTGAATTTAAATTGAATACAGAAGGG_CTCCGGCCCCCGGCCCACCA |
| 5p | 987A | 11708 | 1 | 1 | AAGTTGAATTTAAATTGAATACAGAAGGG_CTGGGGCCCCCGGGGCAGGA |
| 5p | 987A | 11708 | 1 | 1 | AAGTTGAATTTAAATTGAATACAGAAGGA_CTGGGGCCCCCGGGGCAGGA |
| 5p | 987A | 11708 | 1 | 2 | AAGTTGAATTTAAATTGAATACAGAGGG_CTGGGGCCCCCGGGGCAGGA |
| 5p | 987A | 11708 | 1 | 2 | AAGTTGAATTTAAGTTGAATACAGAAGGG_CTGGGGCCCCCGGACAGGA |
| 5p | 987A | 11708 | 1 | 2 | AAGTTGAATTTAAGTTGAATACAGAAGGG_CTGGGGCCCCCGGGGCAGGA |
| 5p | 987A | 11708 | 1 | 3 | AAGTTGAATTTAAATTGAATACAGAAGGG_CTGGGTGGGGGGGGCAGGA |

↑ condense

Continued from Fig. 7A

FIG. 7B

```
                           SEQUENCE LISTING

<160> NUMBER OF SEQ ID NOS: 8

<210> SEQ ID NO 1
<211> LENGTH: 50
<212> TYPE: DNA
<213> ORGANISM: Artificial Sequence
<220> FEATURE:
<223> OTHER INFORMATION: Putative Junction Sequence

<400> SEQUENCE: 1
aagttgtaat ttaaattgaa tacagaaggg ctccggcccc ggcgccacca              50

<210> SEQ ID NO 2
<211> LENGTH: 50
<212> TYPE: DNA
<213> ORGANISM: Artificial Sequence
<220> FEATURE:
<223> OTHER INFORMATION: Putative Junction Sequence

<400> SEQUENCE: 2
aagttgtaat ttaaattgaa tagagaaggg ctccggcccc ggcgccacca              50

<210> SEQ ID NO 3
<211> LENGTH: 50
<212> TYPE: DNA
<213> ORGANISM: Artificial Sequence
<220> FEATURE:
<223> OTHER INFORMATION: Putative Junction Sequence

<400> SEQUENCE: 3
aagttgtaat ttaaattgaa tacagaagga ctccggcccc ggcgccacca              50

<210> SEQ ID NO 4
<211> LENGTH: 50
<212> TYPE: DNA
<213> ORGANISM: Artificial Sequence
<220> FEATURE:
<223> OTHER INFORMATION: Putative Junction Sequence

<400> SEQUENCE: 4
aagttgtaat ttaaattgaa tacagagggg ctccggcccc ggcgccacca              50

<210> SEQ ID NO 5
<211> LENGTH: 50
<212> TYPE: DNA
<213> ORGANISM: Artificial Sequence
<220> FEATURE:
<223> OTHER INFORMATION: Putative Junction Sequence

<400> SEQUENCE: 5
aagttgtaat ttaaattgaa tacagaaggg ctccggcccc ggcaccacca              50

<210> SEQ ID NO 6
<211> LENGTH: 50
<212> TYPE: DNA
<213> ORGANISM: Artificial Sequence
<220> FEATURE:
<223> OTHER INFORMATION: Putative Junction Sequence
```

```
<400> SEQUENCE: 6
aagttgtaat ttaagttgaa tacagaaggg ctccggcccc ggcgccacca        50

<210> SEQ ID NO 7
<211> LENGTH: 50
<212> TYPE: DNA
<213> ORGANISM: Artificial Sequence
<220> FEATURE:
<223> OTHER INFORMATION: Putative Junction Sequence

<400> SEQUENCE: 7
aagttgtaat ttaaattgaa tacagaaggg ctccggtccc ggcgccacca        50

<210> SEQ ID NO 8
<211> LENGTH: 50
<212> TYPE: DNA
<213> ORGANISM: Artificial Sequence
<220> FEATURE:
<223> OTHER INFORMATION: Putative Junction Sequence

<400> SEQUENCE: 8
agttgtaatt taaattgaat acagaagggc tccggccccg gcgccaccaa        50
```

METHODS FOR CHARACTERIZING DNA SEQUENCE COMPOSITION IN A GENOME

CROSS REFERENCE TO RELATED APPLICATIONS

This application is a continuation of U.S. Non Provisional application Ser. No. 15/711,403 filed Sep. 21, 2017, now U.S. Pat. No. 10,487,352 issued Nov. 26, 2019, which is a continuation of U.S. Non Provisional application Ser. No. 14/255,144 filed Apr. 17, 2014, now U.S. Pat. No. 9,797,001 issued Oct. 24, 2017, which claims the benefit of and priority to U.S. Provisional Application Nos. 61/812,876 and 61/813,001 both filed on Apr. 17, 2013, and herein incorporated by reference in their entirety.

FIELD OF THE INVENTION

This invention relates to the field of plant biotechnology. More specifically, the invention relates to a method of determining the composition of a DNA sequence within a plant genome.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 431978seqlist.txt, a creation date of Apr. 17, 2013, and a size of 2 Kb. The sequence listing filed via EFS-Web is part of the specification and is hereby incorporated in its entirety by reference herein.

BACKGROUND OF THE INVENTION

When a plasmid containing a target sequence of interest is transformed into a plant, testing needs to take place to confirm that the transformation has occurred and assess the quality of the transformation. For example, when selecting among multiple plants having been transformed with the same construct, the plant selected should have the intact target sequences of interest without rearrangements, insertions, deletions, or extraneous flanking sequences.

Historically, southern blot methods have been used to confirm the transformation of plasmid constructs and identify potential rearrangement, multi-copy, or partial events. Southern blot experiments can be time-consuming, provide low-resolution, have high cost, and require multiple manual inspections. In addition, southern blot methods are not able to identify the target sequence integration site, nor the flanking sequences of the integration site which are useful for designing an event-specific PCR experiment.

Flanking sequence analysis (FSA) has been successfully used to identify the transgene integration site and to obtain the flanking sequences of the insertion site. Nevertheless, as FSA only targets limited border regions, FSA does not detect potential partial fragments, rearrangements, or truncations beyond the targeted border regions. In addition, the search algorithm utilized by FSA can identify false positives caused by any errors in the reference sequence of the plasmid.

Thus, a continuing need exists for a rapid, low-cost method to effectively characterize the location, number, and integrity of target sequence insertions into plant genomes.

BRIEF SUMMARY OF THE INVENTION

Southern by Sequencing (SbS) is an integrated, high-throughput, sequence and bioinformatic analysis pipeline that assesses and characterizes transformation events for large-scale event selection and advancement decision making. SbS implements a series of filtering strategies to ensure the accuracy and sensitivity of the detection. By starting with a shotgun library enriched for fragments containing the target sequence of interest, SbS can rapidly filter out endogenous reads and identify junction sequences. After junction sequences are identified and extended, the junction is mapped to the plant genome and target sequence construct to determine the location, number, and integrity of the insert sequence. SbS can detect small partial fragments and tolerates errors in the reference sequence of the plasmid.

BRIEF DESCRIPTION OF THE DRAWINGS

FIGS. 7a and 7b describe the process of condensing junction sequences. The first table shows the putative junctions predicted prior to the condense step. The condense script groups all junction-supporting reads based on the 30_20 mer for each junction in the same orientation. For two junctions that are close enough (default distance 2 bp), if the 30_20 mers are identical after shifting the distance, the two junctions are condensed into one. As shown, the two junctions are 11708 and 11709. After being condensed, the junction with more unique supporting reads (junction 11708) takes over the supporting reads from junction 11709. Bolded nucleotides represent Single Nucleotide Polymorphisms (SNPs) and sequences lined out are removed by the split and condense feature of the algorithm.

DETAILED DESCRIPTION

Figure 1:
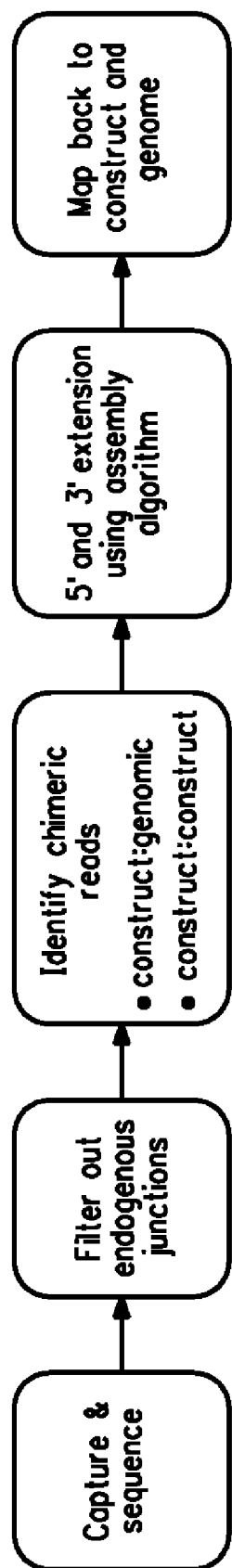
FIG. 1 summarizes the SbS data analysis pipeline.
Figure 2A:
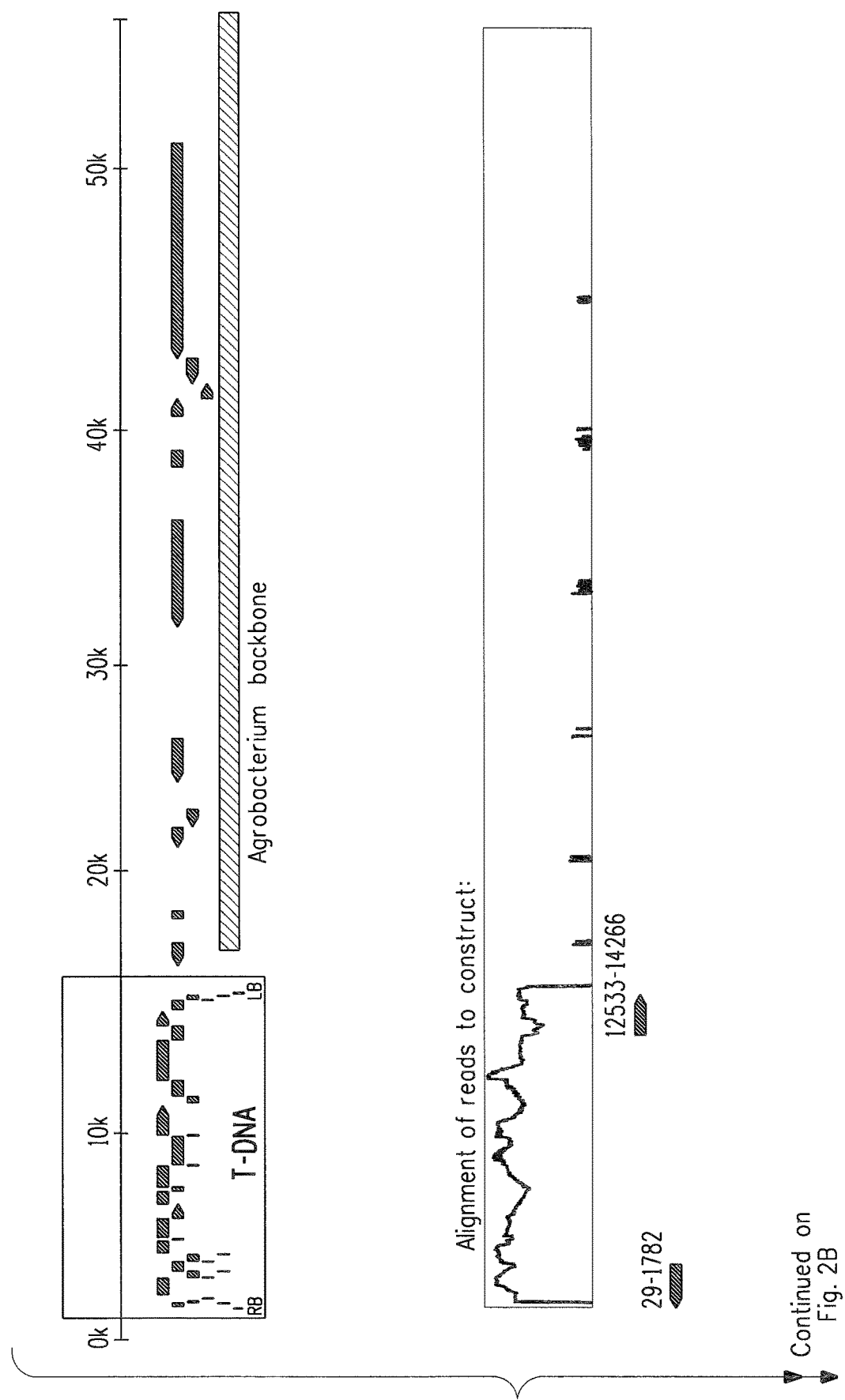
FIGS. 2a and 2b illustrate output data from the SbS pipeline identifying a single insertion of a target sequence of interest on chromosome 2.
Figure 2B:
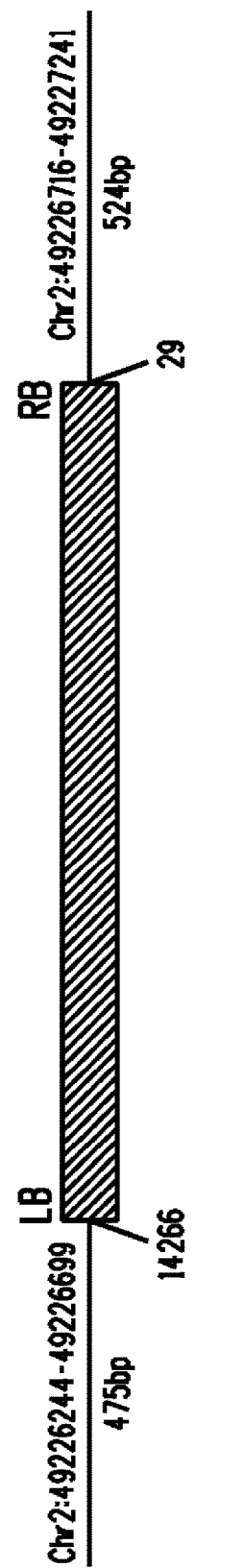
Figure 3A:
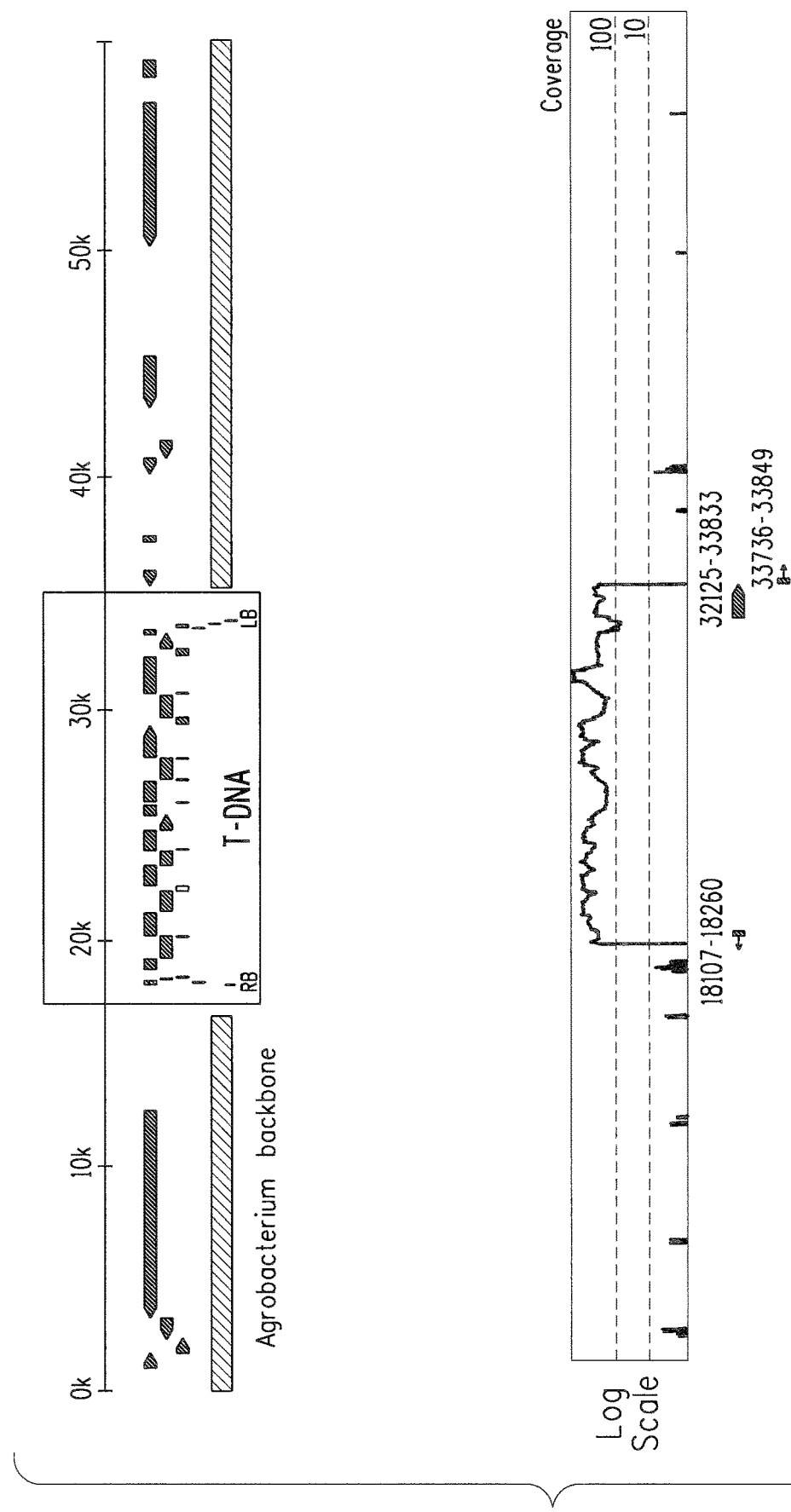
FIGS. 3a and 3b illustrate a single insertion of the target sequence adjacent to an insertion of a fragment of the target sequence. The junction between the target sequence insertion and the target sequence fragment insertion is identified as a construct:construct insertion, while the junctions between the target sequence and the plant genome or the target sequence fragment and the plant genome are identified as construct:genome.
Figure 3B:
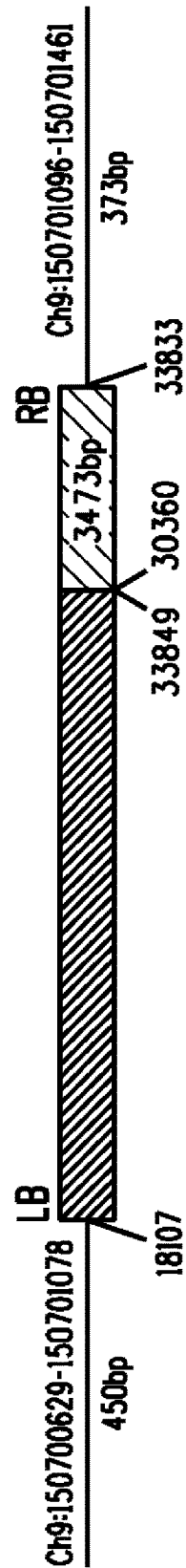
Figure 4A:
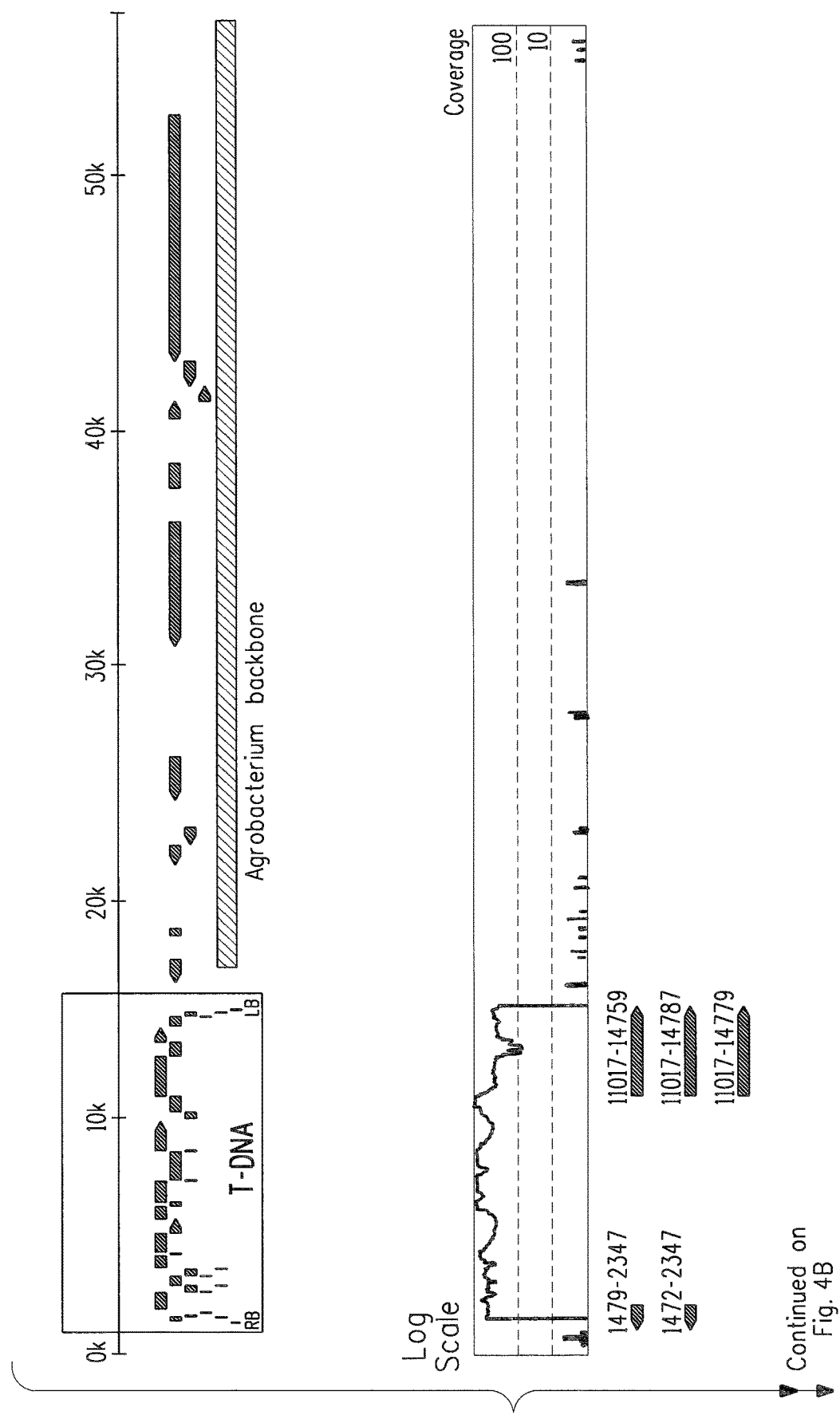
FIGS. 4a and 4b illustrate a complex insertion event, wherein junction sequences were detected on chromosome 6 and chromosome 9. The insertion of the target sequence on chromosome 9 was duplicated and in opposite directions.
Figure 4B:
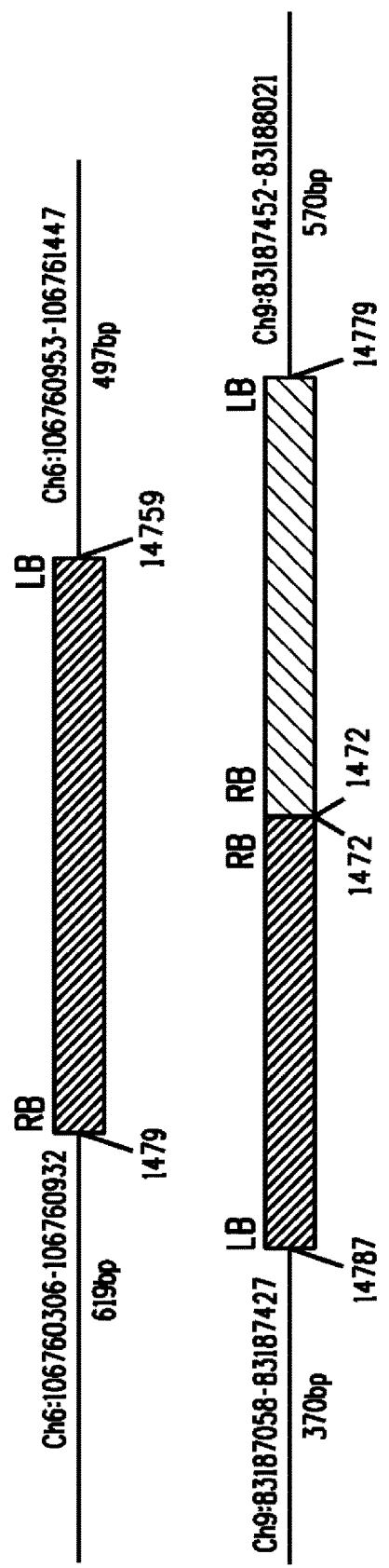
Figure 5:
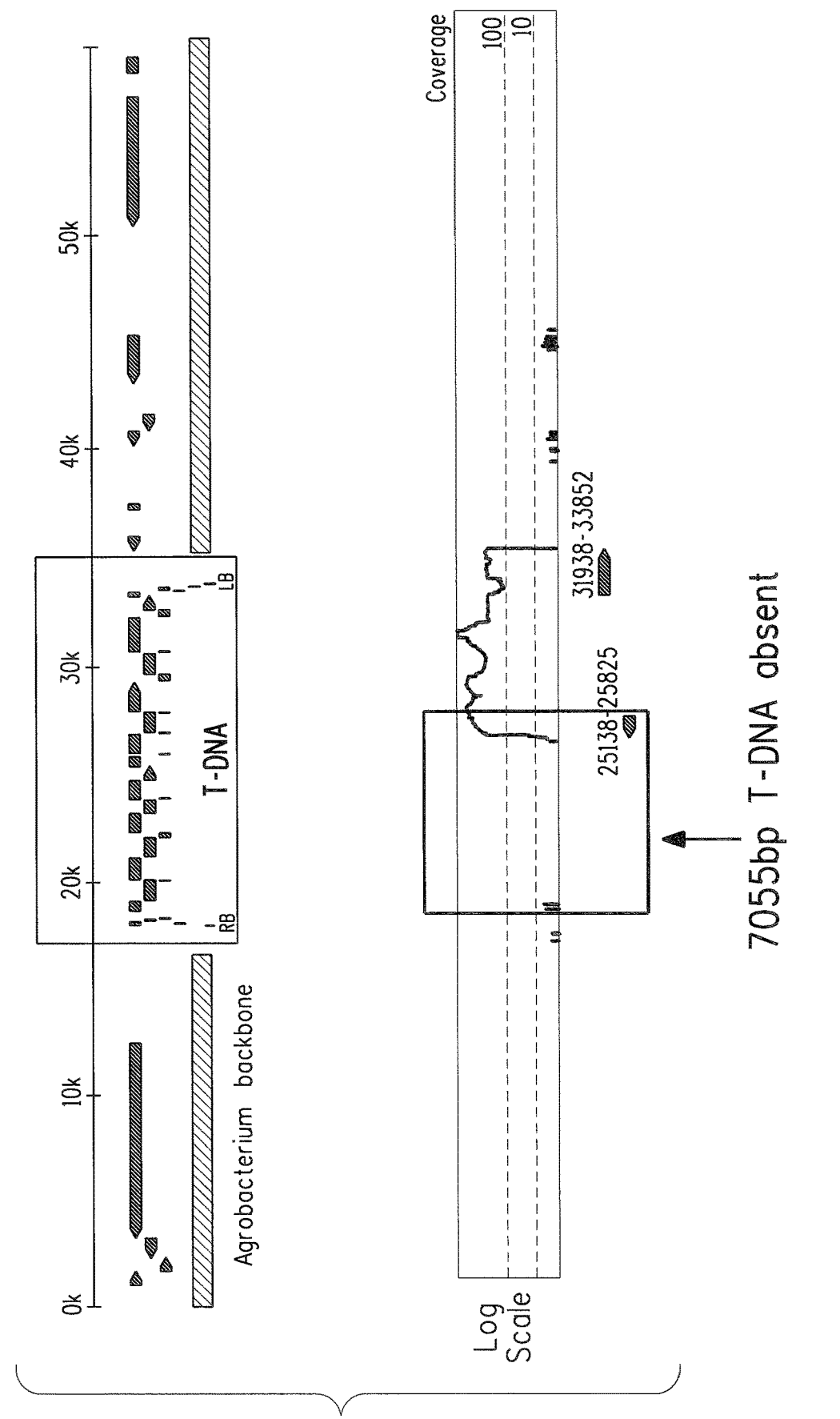
FIG. 5 identifies a truncated insertion of the target sequence, as is evident by the absence of reads aligning to a portion of the target DNA on the *Agrobacterium* construct.
Figure 6:
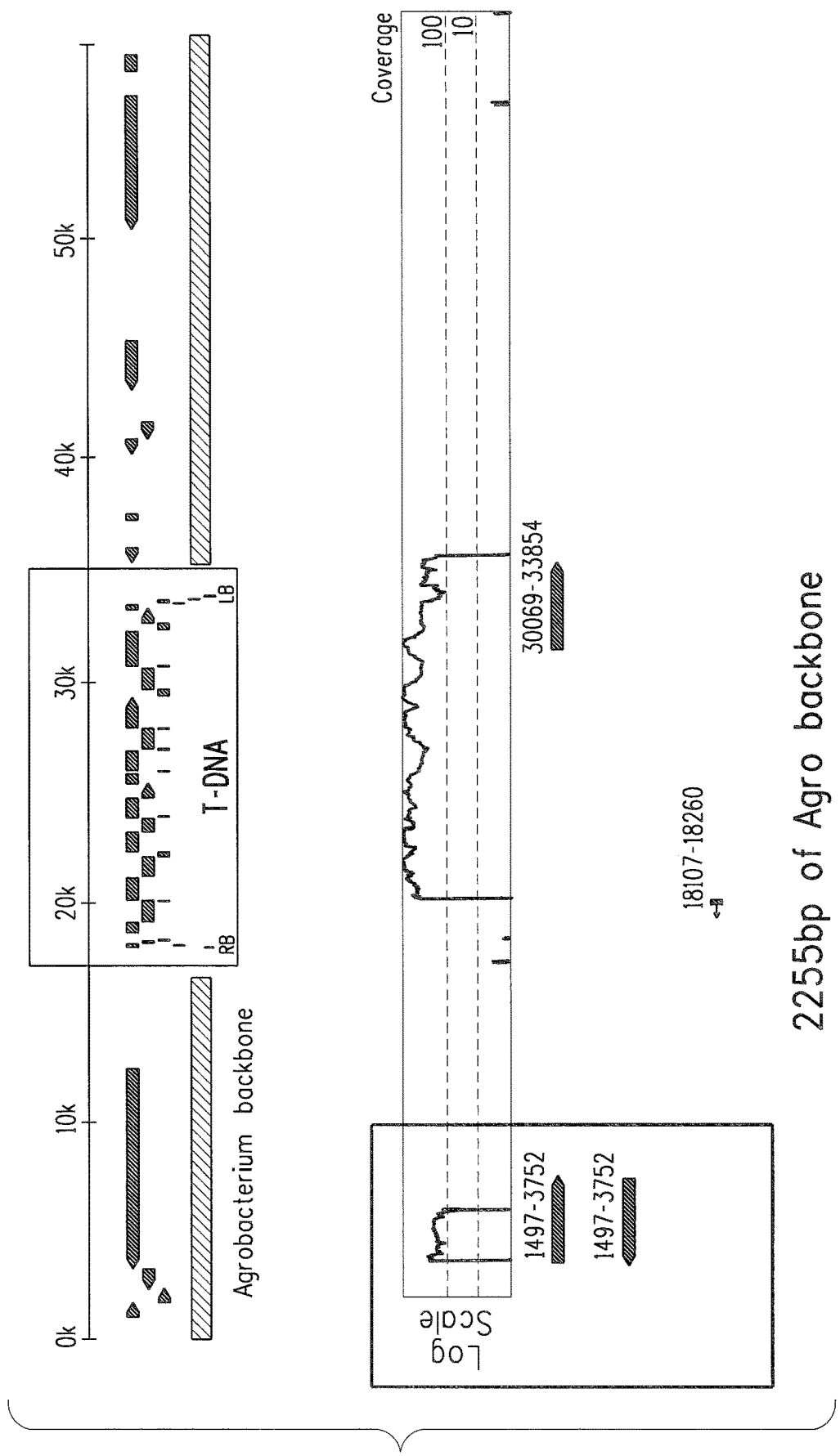
FIG. 6 identifies the insertion of a portion of the *Agrobacterium* backbone into the genome of the plant. Insertion of the *Agrobacterium* backbone can be identified by the alignment of reads (black box) to a portion of the backbone.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed, they are used in a generic and descriptive sense only and not for purposes of limitation.

The characterization of genetically modified crops for commercial product approval currently requires a detailed molecular characterization of the transgenic DNA insert sequence and integrity of the transgene locus. In addition, molecular analysis is a critical component of event selection and advancement decisions during product development.

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al. (1988) Ann. Rev. Genet. 22:421-477). At the same time the presence of the transgene at different locations in the genome will influence the overall phenotype of the plant in different ways. In addition, the copy number of inserted transgenes can affect the phenotype of the plant.

For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct.

Thus, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing or other conventional breeding methods. Progeny of such crosses maintain the transgene expression characteristics of the original transformant. This cross-breeding strategy is used to ensure reliable gene expression in a number of varieties that are well adapted to local growing conditions.

Typically, this molecular analysis has relied on Southern blots to ascertain locus and copy number and targeted sequence of PCR products spanning any inserted DNA to complete the characterization process. The disadvantages of Southern blots include: low throughput, high cost per sample, unknown sequence composition and location, and lack of completeness of detected DNA fragments.

More recently, next generation (NextGen) sequencing and junction sequence analysis via bioinformatics has resulted in both cost and time advantages over Southern blot analysis.

The invention relates to the amplification or capture of target sequences, pooling amplified or captured sequence and the characterization of the pooled sample by DNA sequencing. DNA sequence data is assembled and compared to a reference sequence. It is useful for the characterization of transgene insertions in plants, animals, and microbial species; human disease diagnostics, genomic location of single or multiple copies of target sequence, and purity testing.

The invention further relates to a method of bioinformatics analysis and characterization of target sequences of interest in the genome of a plant. When combined with the novel amplification and capture methods of the invention, this characterization is called Southern by Sequencing (SbS). As used herein, the term "Southern by Sequencing" refers to a sequential series of steps that captures and amplifies DNA, pools the samples, and analyzes that sequence data to characterize in vivo structure.

The articles "a" and "an" are used herein to refer to one or more than one (i.e., to at least one) of the grammatical object of the article. By way of example, "an element" means one or more than one element.

Throughout the disclosure, various terms of art will be used and are herein defined:

A DNA "construct" is an assembly of DNA molecules linked together that provide one or more expression cassettes. The DNA construct may be a plasmid that is enabled for self-replication in a bacterial cell and contains various endonuclease enzyme restriction sites that are useful for introducing DNA molecules that provide functional genetic elements, i.e., promoters, introns, leaders, coding sequences, 3' termination regions, among others; or a DNA construct may be a linear assembly of DNA molecules, such as an expression cassette. The expression cassette contained within a DNA construct comprises the necessary genetic elements to provide transcription of a messenger RNA. The expression cassette can be designed to express in prokaryote cells or eukaryotic cells. Expression cassettes of the embodiments of the present invention are designed to express in plant cells.

A "transgene" is a gene that has been introduced into the genome by a transformation procedure. The site in the plant genome where a recombinant DNA has been inserted may be referred to as the "insertion site" or "target site".

When recombinant DNA is introduced into a plant through traditional crossing, its flanking regions will generally not be changed A "flanking region" or "flanking sequence" as used herein refers to a sequence of at least 20 bp, preferably at least 50 bp, and up to 5000 bp, which is located either immediately upstream of and contiguous with, or immediately downstream of and contiguous with, the original foreign insert DNA molecule.

As used herein, "insert DNA" refers to the heterologous DNA within the expression cassettes used to transform the plant material while "flanking DNA" can be made up of either genomic DNA naturally present in an organism such as a plant, or foreign (heterologous) DNA introduced via the transformation process which is extraneous to the original insert DNA molecule, e.g. fragments associated with the transformation event.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extrachromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that includes the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) Meth. Enzymol. 143:277) and particle-accelerated or "gene gun" transformation technology (Klein et al. (1987) Nature (London) 327:70 73; U.S. Pat. No. 4,945,050, incorporated herein by reference).

Transformants contain unique junctions between a piece of heterologous insert DNA and genomic DNA, or two (2) pieces of genomic DNA, or two (2) pieces of heterologous DNA. A "junction" is a point where two (2) specific DNA fragments join. For example, a junction exists where insert DNA joins flanking DNA. A junction point also exists in a transformed organism where two (2) DNA fragments join together in a manner that is modified from that found in the native organism. "Junction DNA" refers to DNA that comprises a junction point.

"PCR" or "polymerase chain reaction" is a technique used for the amplification of specific DNA segments (see, U.S. Pat. Nos. 4,683,195 and 4,800,159; herein incorporated by reference). In a PCR protocol, oligonucleotide primers can be designed for use in PCR reactions to amplify (or "capture") corresponding DNA sequences from cDNA or genomic DNA extracted from any organism of interest. Methods for designing PCR primers and PCR cloning are well known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target nucleic acid sequence, e.g., by PCR or other conventional nucleic-acid amplification methods Probes and primers are of sufficient nucleotide length to bind to the target DNA sequence specifically in the hybridization conditions or reaction conditions determined by the operator. This length may be of any length that is of sufficient length to be useful in a detection method of choice. Generally, 11 nucleotides or more in length, 18 nucleotides or more, and 22 nucleotides or more, are used. Such probes and primers hybridize specifically to a target sequence under high stringency hybridization conditions. Probes and primers according to embodiments of the present invention may have complete DNA sequence similarity of contiguous nucleotides with the target sequence, although probes differing from the target DNA sequence and that retain the ability to hybridize to target DNA sequences may be designed by conventional methods. Probes can be used as primers, but are generally designed to bind to the target DNA or RNA and are not generally used in an amplification process.

Specific primers can be used to amplify an integration fragment to produce an amplicon that can be used as a "specific probe" for identifying events in biological samples. When the probe is hybridized with the nucleic acids of a biological sample under conditions which allow for the binding of the probe to the sample, this binding can be detected and thus allow for an indication of the presence of the event. Such identification of a bound probe has been described in the art. In an embodiment of the invention the specific probe is a sequence which, under optimized conditions, hybridizes specifically to a desired region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the event.

A "target sequence of interest" can be any nucleotide sequence, native or non-native, integrated, or partially integrated, into the genome of a plant. In certain embodiments, the target sequence of interest is a heterologous sequence. "Heterologous" in reference to a polynucleotide sequence is a sequence that originates from a foreign species or artificial source, or, if from the same species, is substantially modified from its native form in composition and/or genomic locus by deliberate human intervention. A target sequence of interest can include, but is not limited to: transgenes, native traits, or natural or induced mutations.

Target sequences of interest can be reflective of the commercial markets and interests of those involved in the development of the crop. Crops and markets of interest change, and as developing nations open up world markets, new crops and technologies will emerge. In addition, as our understanding of agronomic traits and characteristics such as yield and heterosis increase, the choice of target sequences for transformation will change accordingly. General categories of target sequences of interest include, for example, those target sequences involved in information, such as zinc fingers, those involved in communication, such as kinases, and those involved in housekeeping, such as heat shock proteins. More specific categories of target sequences, for example, include polynucleotides encoding important traits for agronomics, insect resistance, disease resistance, herbicide resistance, sterility, grain characteristics, and commercial products. Target sequences of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important target sequences encode latex, Floury 2, growth factors, seed storage factors, and transcription factors.

Insect resistance target sequences may encode resistance to pests that have great yield drag such as rootworm, cutworm, European Corn Borer, and the like. Such polynucleotides include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Target sequences encoding disease resistance traits include detoxification genes, such as against fumonosin (U.S. Pat. No. 5,792,931); avirulence (avr) and disease resistance (R) polynucleotides (Jones et al. (1994) *Science* 266:789; Martin et al. (1993) *Science* 262:1432; and Mindrinos et al. (1994) *Cell* 78:1089); and the like.

Herbicide resistance traits may include target sequences coding for resistance to herbicides that act to inhibit the action of acetolactate synthase (ALS), in particular the sulfonylurea-type herbicides (e.g., the acetolactate synthase (ALS) polynucleotide containing mutations leading to such resistance, in particular the S4 and/or Hra mutations), target sequences coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such polynucleotides known in the art. The bar gene encodes resistance to the herbicide basta, the nptII gene encodes resistance to the antibiotics kanamycin and geneticin, and the ALS-gene mutants encode resistance to the herbicide chlorsulfuron.

Target sequences further include sterility genes. Sterility genes can provide an alternative to physical detasseling. Examples of polynucleotides used in such ways include male tissue-preferred genes and genes with male sterility phenotypes such as QM, described in U.S. Pat. No. 5,583,210. Other target sequences include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a target sequence that could increase for example, starch for ethanol production, or provide expression of proteins. Another important commercial use of transformed plants is the production of polymers and bioplastics such as described in U.S. Pat. No. 5,602,321. Target sequences such as β-Ketothiolase, PHBase (polyhydroxyburyrate synthase), and acetoacetyl-CoA reductase (see Schubert et al. (1988) *J. Bacterial.* 170:5837-5847) facilitate expression of polyhyroxyalkanoates (PHAs).

The methods described herein can be employed to characterize the number, location, and integrity of target sequences in the genome of any plant of interest. In order to obtain sequence reads suitable for analysis in the bioinformatic pipeline, multiple fragments of DNA specific for the target sequence and corresponding junction sequences must be sequenced. DNA fragments corresponding to the sequence of interest and/or endogenous genomic DNA can be prepared for sequencing by any method suitable for high-throughput sequencing of short fragments. In some embodiments, DNA fragments are prepared using a shotgun cloning strategy to generate template for high-throughput dideoxynucleotide sequencing or next generation sequencing.

In order to prepare a DNA shotgun library for sequencing, genomic DNA from a sample plant must be collected and isolated. As used herein, the term "sample plant" refers to any plant having a sequence of interest. In some embodiments, the sequence of interest is heterologous to the sample plant. Thus, the methods disclosed herein are useful for detecting the presence of a sequence of interest in a sample plant. Generally, the isolation of plant genomic DNA results in obtaining purified plant DNA which is free of lipids, proteins and other cellular debris. Preferred plant DNA isolation methods include: lysis, heating, alcohol precipitation, salt precipitation, organic extraction, solid phase extraction, silica gel membrane extraction, CsCl gradient purification, and any combinations thereof. In some embodiments genomic DNA can be isolated from the sample plant by the CTAB (cetyltriethylammonium bromide, Sigma H5882) method described by Stacey & Isaac (1994 In Methods in Molecular Biology Vol. 28, pp. 9-15, Ed. P. G. Isaac, Humana Press, Totowa, N.J.), the Omega Biotek (Norcross, Ga.) EZNA Plant 96 kit, or the silica-gel-membrane technology marketed as the DNeasy kit (Qiagen, Valencia, Calif.). Following isolation, genomic DNA from the sample plant is sheared to provide multiple fragments of genomic DNA suitable for library construction. Shearing of plant DNA can be accomplished with sonication, enzymatically, with heat, or any other method suitable for production of genomic DNA fragments fit for shotgun library construction. In one embodiment, the genomic DNA is sheared by sonication.

In some embodiments, genomic DNA from the sample plant is sheared by sonication, end repaired, A-tailed, and ligated to adapter sequences. Fragment ends can be repaired and A-tailed using any method in the art suitable for high-throughput sequencing. In certain embodiments, adapters are ligated to the ends of sheared genomic DNA to enable sample pooling at the hybridization and sequencing stages. Following ligation to adapter sequences, genomic DNA fragments can be amplified by PCR. For example, DNA fragments with adapter sequences can be amplified by 5, 6, 7, 8, 9, 10, 12, 15, or any number of PCR cycles to yield the desired quantity of amplified genomic fragment for sequencing.

In certain embodiments, sequence capture can be used to enrich the pool of genomic DNA fragments for those containing regions of the target sequence of interest. As used herein, the term "enrich" or "enriching" refers to an increase in concentration of a particular group of genomic DNA fragments. For example, after enriching for DNA fragments having regions of the target sequence of interest, the fragment library will contain a higher proportion of fragments having regions of the target sequence of interest than prior to the enriching process. As used herein, the term "regions of the target sequence" refers to any polynucleotides corresponding to in the target sequence. In certain embodiments, regions of the target sequence comprise at least 2, at least 5, at least 10, at least 15, at least 20, at least 25, at least 30, at least 35, at least 40, at least 45, at least 50, at least 60, at least 70, at least 80, at least 90, at least 100, at least 125, at least 150, at least 175, at least 200, at least 225, at least 250, at least 275, at least 300, at least 350, or at least 400 consecutive nucleotides corresponding to in the target sequence of interest.

"Sequence capture" refers to a process of selecting particular DNA fragments from a DNA library using probes specific for the polynucleotide of interest. In some embodiments, probes are designed as unique sequences representing all nucleotides of the target sequence. Any number of probes can be used in the methods disclosed herein, and the number of probes will vary with the length of the target sequence. For example at least 2, at least 25, at least 50, or about 100, about 200, about 300, about 400, about 500, about 750, about 1000, about 1500, about 2000, about 3000, about 4000, about 5000, about 10,000, about 50,000, about 100,000, about 250,000, about 500,000, about 750,000, or about 1,000,000 unique probes can be designed to cover the complete length of a target sequence of interest. In some embodiments, probes are modified to contain features facilitating subsequent capture and purification of probe/DNA fragment complexes. For example, in some embodiments probes are modified to have a biotin label that can later be captured with streptavidin beads. Sequences can also be captured and enriched using microarray slides having probes attached to the surface.

Sequence capture based methods can be used to enrich the DNA fragment library for those fragments containing a region of the target sequence of interest. Sequence capture methods can be performed according to standard protocols available at the Roche NimbleGen website located at www.nimblegen.com. Briefly, DNA shotgun libraries are denatured in a cocktail with hybridization buffers, such as the SeqCap EZ Developer Reagent, and blocking oligos corresponding to any adapter sequences used in the construction of the library. After denaturation, the cocktail is combined with a biotinylated probe library and incubated to allow hybridization of the probe library with the genomic fragment library. After hybridization, the cocktail is combined with streptavidin beads and subsequently washed and eluted to provide bound DNA fragments having homology to the target sequence of interest. In one embodiment, the washed and eluted libraries can be amplified by undergoing 3, 4, 5, 6, 7, 8, 9, 10, 12, 15 or any number of amplification cycles (e.g., PCR) to provide sufficient quantity of DNA for sequencing or further rounds of sequence capture. Thus, in some embodiments, multiple rounds of sequence capture can be used in order to further enrich the DNA fragment library for fragments having a region of the target sequence of interest. For example 2 rounds, 3 rounds or 4 rounds of sequence capture can be performed using probes having homology to the target sequence of interest.

Following the final round of sequence capture, the DNA fragment library can be pooled, amplified, and purified in preparation for high-throughput sequencing. For example, the DNA fragment library can be amplified by 5, 6, 7, 8, 9, 10, 12, 15, 17, 20, 25, or any number of amplification cycles (e.g., PCR) to provide sufficient quantity of DNA for sequencing. The DNA fragment library can be purified by any method known in the art (e.g. Qiagen Qiaquick columns).

After selecting for those DNA fragments having a region of the target sequence of interest, the DNA fragment library can be sequenced using any method known in the art. In some embodiments, the DNA fragment library can be sequenced by next generation sequencing. The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. In particular embodiments, the DNA fragment library is sequenced using the Illumina MiSeq or HiSeq 2500 system.

Sequencing of the DNA fragment library will result in a collection of individual sequences corresponding to the selected DNA fragments having regions of the target sequence of interest. As used herein, the term "read" refers to the sequence of a DNA fragment obtained after sequencing. In some embodiments, sequencing produces about 500,000, about 1 million, about 1.5 million, about 2 million, about 2.5 million, about 3 million, or about 5 million reads from the DNA sequence library. In certain embodiments, the reads are paired-end reads, wherein the DNA fragment is sequenced from both ends of the molecule.

In one embodiment, the method utilizes construct-specific PCR primers and next generation (NextGen) sequencing technology to characterize transgene events. Sequence reads generated from this method can be used for, but not limited to: identifying insertion site, transgene integrity, and transgene copy number.

Genomic DNA may be isolated and purified using any technique known in the art. For transgenic plant analysis, one benefit of the method is that sufficient genomic DNA may be obtained via leaf punch, single leaf, or leaf part, or other sample that allows the plant to continue normal growth and development. The isolated genomic DNA can then be purified and analyzed for quality and quantified using any method known in the art, such as, for example with a Fragment Analyzer™ (Advanced Analytical, Ames, Iowa).

The genomic DNA is then sheared into fragments using any of several techniques known in the art into any convenient fragment size using any protocol known in the art such as, for example, with a Covaris E210™ (Covaris Inc, Woburn Mass.). Sizes of fragments may range from about 50 base pairs to about 2.5 kb in length including, but not limited to: 75, 100, 150, 200, 250, 300, 350, 400, 450, 500, 550, 600, 650, 700, 750, 800, 850, 900, 950, or 1 kb in length; or about 1.25, 1.5, 1.75., 2.0, or 2.5 or greater kb in length or any length within these ranges. The sheared fragments are then end-repaired, A-tailed, and ligated to specialized adapters by any protocol known in the art such as, for example, the protocol provided by Kapa Biosystems™ (Woburn Mass.).

The adapters are designed with ninety-six unique six-base-pair segments called a "barcode" also known as "tags", "multiplex identifiers", "indexes", or "index" sequence. These barcodes serve as unique identifiers and assist in sequence analysis. Together, the DNA fragments with attached barcodes form fragment libraries that can be enriched via PCR amplification with construct- and adapter-specific PCR primers.

The sensitivity and specificity of the method can be adjusted and is determined by the design of the construct-specific PCR primers along the length of the construct and adapter sequence. Two primers are designed for every 200 base pairs on alternating strands, or 400 base pairs on a single strand. The primers may be nested or overlapping depending on the resolution desired.

The primary round of PCR utilizes a first primer (can be of a nested pair) targeted to the construct sequence, and an adapter-specific primer as the reverse primer, thus anchoring one end of each resulting amplicon. A secondary round of PCR pairs the adapter specific primer with the nested PCR primer. The nested PCR primer can include a sequence tag related to the sequencing platform that will be used for sequencing and analysis. For example, the Illumina P5™ sequence for use on Illumina™ sequencing systems.

Following PCR, the fragment libraries can be purified by any protocol known in the art, such as for example, Ampure Beads™ (Beckman Genomics, Danvers, Mass.) and analyzed for PCR artifacts. The libraries are pooled in equal molar ratios and diluted to the preferred concentration for sequencing. In another embodiment, the libraries can be pooled in any manner that would achieve appropriate sequencing data.

In a further embodiment, the method utilizes a biotinylated probe library of the transgene construct of interest which is analyzed as a collection and reduced to a set of unique sequences representing all bases within the collection. The DNA probe library is designed such that nearly all bases within a construct pool will be targeted during an enrichment step described herein. The probe library is kept in solution as opposed to being placed on a glass slide or plate microarray.

Genomic DNA is isolated from biological samples and sheared and ligated to adapters as above. The ligated fragments are then amplified through up to eight rounds of PCR. These amplified libraries can be assessed for quality and PCR artifacts, then pooled into equal molar ratios in groups of 24, 48, or 96 or other groups according to operator preference, and diluted to a working stock of preferred ng/µl.

The amplified libraries are denatured with hybridization buffers, developer reagents and blocking oligos corresponding to the adapter sequences. After denaturation, the pools are combined with the biotinylated probes and incubated at 47° C. for 16 hours. Following hybridization, the solution is bound to streptavidin beads and washed.

Washed and eluted pools are PCR amplified for up to five cycles, purified and amplified again. The final library pools are quantified and diluted for sequencing.

One benefit of this embodiment is that samples from several diverse events and organisms may be pooled and analyzed at once. This embodiment can catch anomalies not detected by QT-PCR or Southerns.

Sequencing reads obtained from sequencing a DNA fragment library selected for genomic DNA fragments having regions of the target sequence of interest can be processed in a high-throughput manner in order to characterize transformation events in a sample plant. In some embodiments, the reads obtained from sequencing are post-processed to remove any adapter sequences. For example, the sequence of any adapter sequences, such as NEXTFlex adapter sequences, can be searched for and removed from the ends of any reads containing a minimum of 3 bp of the sequences. The collection of reads can also be processed to remove low quality sequence using a Kmer analysis to maximize the specificity and sensitivity of the selected reads. The collection of reads is pushed through an internal Kmer analysis pipeline which utilizes Jellyfish (see the website at bioinformatics.oxfordjournals.org/content/27/6/764) for K-mer counting. Reads with k-mer (default: 31-mer) counts of less than or equal to 2 are removed from downstream analysis. Reads can also be post-processed to select the top 60% most abundant reads for further analysis in the methods disclosed herein. Alternatively, the top 40%, 45%, 50%, 55%, 65%, 70%, 75%, 80%, 85%, 90%, 95% or 100% of the reads can be selected for further analysis. In specific embodiments the top 60% reads is the appropriate selection to maximize sensitivity for a reasonable specificity of junction detection. The top 60% can be appropriate for total read counts of 1-2 million for constructs of about 50 Kb long (T-DNA size of about 20 Kb). As the targeting read depth changes, the 60% value can change. In order to select the optimum number of reads for further analysis, the background, specificity, sensitivity, and quality of the reads should be considered.

In order to exclude any endogenous reads from further analysis, reads can be aligned to the genome of a control plant. As used herein, the genome of a "control plant" refers to the genome of a plant of the same or phylogenically similar genotype not having the target sequence of interest. Any reads aligning to the genome of a control plant are considered "endogenous reads" and excluded from further analysis in the methods disclosed herein. That is, reads that correspond to at least a portion of the target sequence are selected for further analysis in the SbS pipeline.

Methods of alignment of sequences for comparison are well known in the art. Thus, the alignment of any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine optimum alignment. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mot. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990)*J. Mol. Biol.* 215:403 are based on the algorithm of Karlin and Altschul (1990) supra. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences) can be used. See the website at www.ncbi.nlm.nih.gov. Bowtie2 (locate at the website nature.com/nmeth/journal/v9/n4/full/nmeth.1923.html) and BWA (located at the website at ncbi.nlm.nih.gov/pubmed/19451168) can also be used to efficiently align millions of short reads generated by NGS to a genome. In another embodiment, GSNAP (Thomas D. Wu, Serban Nacu "Fast and SNP-tolerant detection of complex variants and splicing in short reads. *Bioinformatics*. 2010 Apr. 1; 26(7):873-81. Epub 2010 Feb. 10) can also be used.

Algorithms and parameters for alignment can be adjusted depending on the type of plant selected, the type of target sequence being characterized, and the method of transformation used to introduce the target sequence into the sample plant.

Reads having some alignment to the target sequence of interest are then aligned with each other to identify junction sequences. In order for reads to have some alignment to a target sequence of interest, the read must have about 2, about 4, about 6, about 8, about 10, about 12, about 15, about 20, or about 30 nucleotides in common with the target sequence, or share at least about 50%, about 60%, about 70%, about 75%, about 80%, about 85%, about 90%, about 95%, or about 100% homology with the target sequence of interest over a fragment of the target sequence about 5, about 10, about 15, about 20, about 25, about 30, about 35, about 40, about 45, about 50, about 75, or about 100 consecutive nucleotides in length. As used herein, a "junction" refers to the point where two different fragments of DNA join together. For example, a junction can exist between insert DNA (e.g. plasmid, target sequence, etc.) and genomic DNA of a sample plant, or between two insert DNA sequences. A junction also exists in a transformed plant where two DNA fragments join together in a manner that is modified from that found in the native plant. "Junction sequence" refers to a segment of DNA comprising a junction. Junction sequences can be about 5, about 7, about 10, about 12, about 15, about 17, about 20, about 25, about 26, about 27, about 28, about 29, about 30, about 31, about 32, about 33, about 34, about 35, about 40, about 50, about 60, about 75, about 100, or about 5-10, 10-15, 10-20, 10-30, 10-40, 20-40, or 25-35 nucleotides in length.

Junction sequences can be identified by aligning reads and identifying the junction where the read no longer aligns to the target sequence. Due to the nature of alignment algorithms, junctions are sometimes predicted close to each other. When junctions are predicted within about 5, about 4, about 3, about 2, or about 1 nucleotide from each other, the junctions can be condensed. As used herein, the terms "condensed" or "condense" refer to the process of combining similar junction predictions into a single consensus junction sequence. In order to condense junction sequences, a fragment of each read surrounding the predicted junction sequence are aligned. After alignment, the junction with more unique supporting reads is identified as the junction. In some embodiments, fragments of reads surrounding the predicted junction sequence are comprised of thirty (30) nucleotides of genomic DNA and twenty (20) nucleotides of target sequence. This could also be about 10, 15, 20, 25, 30, 35, 40, 45, 50, 60, 70, 80, 90 or to 100 nucleotides of genomic DNA sequence and from about 10, 15, 20, 25, 30, 35, 40, 45, 50, 60, 70, 80, 90 or to 100 nucleotides of target sequence. As used herein, a DNA fragment comprising thirty (30) nucleotides of genomic DNA and twenty (20) nucleotides of target sequence is referred to as a "30_20 mer." Condensing is useful to remove junction reads having sequencing errors.

In some embodiments, a junction sequence is identified and the 30_20 mer junction sequence is extended in order to facilitate genomic mapping. Junction sequences can be extended by using a sequence assembly tool, such as S SAKE (Warren R., et al. (2007) *Bioinformatics* 23(47): 500-501), herein incorporated by reference. In certain embodiments, read data from genomic library sequencing, or existing genomic sequence data for the control plant, can be assembled to the ends of the junction sequence in order to obtain the extended junction sequence. As used herein, a "contig" refers to the extended junction sequence.

Contigs can be mapped to the genome of a control plant and to the target sequence of interest in order to identify the number, location, and integrity of the target sequence insertions into the genome of the sample plant. The number of target sequences can be determined by the number of junction sequences identifying a junction between the target sequence and the plant genome, along with the number of junction sequences between two target sequences. For example, if a junction was identified on each end of the target sequence between the target sequence and the plant genome, only one copy of the target sequence would be expected in the plant genome. However, if further junctions sequences were detected between two insert sequences, then multiple target sequences would be expected. The integrity of the target sequence insertion can be evaluated by analyzing read alignments to the target sequence to identify insertions, deletions, or rearrangements of the target sequence of interest. For example, SNPs within the target sequence can be identified and *Agrobacterium* backbone contamination can be detected. Contigs can be mapped to the genome of a control plant in order to identify the location of the target sequence insertion.

Plants for use in the methods disclosed herein include whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

The methods disclosed herein can be used to characterize target sequences of interest in any plant species, including, but not limited to, monocots and dicots. Examples of plant species of interest include, but are not limited to, corn (*Zea mays*), *Brassica* sp. (e.g., *B. napus, B. raga, B. juncea*), particularly those *Brassica* species useful as sources of seed oil, alfalfa (*Medicago sativa*), rice (*Oryza* saliva), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos mucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In some embodiments, a sample plant is selected for advancement and breeding based on the number, location, integrity, or any combination thereof, of the target sequence of interest in the genome of the sample plant. The sample plant can be selected for use in a breeding program such as pedigree breeding, recurrent selection, mass selection, or mutation breeding.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

EXPERIMENTAL

Example 1: Tiling Method

Using sequence information from the transgene construct, construct-specific ligation mediated nested PCR (LMN-Tiling primers were designed. Assay sensitivity and specificity was determined by the nested PCR primer design, in which two primers were designed for every 200 base pairs on alternating stands, or 400 base pair spacing on a single strand.

Following primer design, DNA was extracted from lyophilized leaf punches using the EZNA Plate 96™ kit (Omega Biotek, Norcross, Ga.). Purified genomic DNA was assessed for quality and quantity with a Fragment Analyzer™ (Advanced Analytical, Ames, Iowa) and subsequently sheared to an average fragment size of 1500 base pairs with a Covaris E210™ (Covaris Inc, Woburn, Mass.). Sheared DNA was end repaired, A-Tailed, and ligated according to the protocols provided by Kapa Biosystems™ (Woburn, Mass.). Ligated adapters were custom designed with ninety-six unique, six base-pair barcodes and linked to the Illumina P7™ sequence to enable Illumina sequencing post-PCR.

Following ligation, fragment libraries were enriched for transgene sequences by two rounds of twenty cycle amplification. Primary PCR utilized the first primer of the nested pair as the forward primer and an adapter-specific primer as the reverse primer, anchoring one end of each amplicon. Secondary PCR paired the adapter-specific primer with the nested PCR primer, which includes the Illumina P5™ sequence, finishing the fragments for Illumina™ sequence. Following purification with AmpureXP™ beads (Beckman Genomics, Danvers, Mass.), fragment libraries were analyzed on the Fragment Analyzer™, pooled in equal molar ratios into ninety six sample pools and diluted to 2 nM. Pools were sequenced on the Illumina (San Diego, Calif.) MiSeq or HiSeq 2500™ system, generating one to two million 100 base pair paired end reads per sample as per manufacturer protocols.

Generated sequence was used to identify insertion site, transgene integrity and transgene copy number.

Example 2: Southern by Sequencing Method

The Southern by Sequencing (SbS) application employs a sequence capture based method to enrich Illumina™ sequencing libraries for construct containing fragments. The first step in this process was to design a biotinylated probe library which was synthesized by Roche NimbleGen™ (Madison, Wis.) after approval by the Pioneer design team. Transgene constructs of interest were analyzed as a collection and reduced to a set of unique sequences representing all bases within the collection. A DNA probe library was designed such that nearly all bases within a construct pool were targeted during the enrichment process.

Following probe library design, next generation DNA shotgun libraries were produced for individual events via standard molecular manipulations. In brief, DNA was isolated from leaf punches via Omega Biotek (Norcross, Ga.) EZNA Plant 96™ kit. Purified genomic DNA was assessed for quality and quantity with a Fragment Analyzer™ (Advanced Analytical, Ames, Iowa) and subsequently sheared by sonication to an average fragment size of 400 bp with a Covaris E210™ (Covaris Inc, Woburn, Mass.). Sheared DNA was end repaired, A-Tailed, and ligated according to the protocols provided by Kapa Biosystems™ (Woburn, Mass.).

The ligated BIOO Scientific (Austin, Tex.) NEXTFlex™ adapter sequences included ninety six unique six base pair bar-codes flanked by Illumina™ specific sequences, to enable sample pooling at the hybridization and sequencing stages.

These molecular barcodes (also known as tags, indexes or multiplex identifiers) are short DNA sequences that appear at the ends (5" or 3") of every sequencing read, and function to link a read to its library source. To support efficient pooling of samples, we incorporated index barcodes into the Illumina library construction process by adding them into Illumina's I5™ adapter and utilizing the standard Illumina barcodes in Illumina's I7™ adapter. Pared with Illumina's 17 adapter barcodes, of which there are currently 24, this provided the means to run 2,304 samples together with a unique barcode identifier on each sample.

Ligated fragment libraries were amplified eight cycles according NimbleGen™ capture protocols. Amplified libraries were once again assessed for quality and quantity with the Advanced Analytical Fragment Analyzer™, pooled in equal molar ratios in groups of 24, 48, or 96 and diluted to a working stock of 5 ng/ul.

Sequence enrichment was accomplished according to the NimbleGen™ protocols, utilizing a double capture approach to increase on target reads. DNA shotgun libraries described above were denatured in a cocktail with hybridization buffers, SeqCap EZ Developer Reagent™, and blocking oligos corresponding to the adapter sequences in the pool. Post denaturation, the cocktail was combined with the biotinylated oligo library and incubated at forty seven degrees Celsius for sixteen hours. Following the hybridization, the cocktail was mixed with streptavidin Dyanbeads M-270™ (LifeTech, Grand Island, N.Y.). Using the DynaMag-2™ (LifeTech, Grand Island, N.Y.) the bound DNA fragments were washed according to the NimbleGen™ capture protocol. Washed and eluted library pools were amplified five cycles, purified according to manufacturer instructions with Qiagen (Germantown, Md.) Qiaquick™ columns, and then captured, amplified sixteen cycles, and purified a second time using the methods described above.

Final capture library pools were quantified with the Agilent tape station and diluted to 2 nM for sequencing. Pools were sequenced on the Illumina™ (San Diego, Calif.) MiSeq™ or HiSeq 2500 System™, generating one to two million 100 base pair paired-end reads per sample.

Generated sequence was used to identify insertion site, transgene integrity and transgene copy number.

Example 3: Southern by Sequencing Bioinformatic Pipeline

SbS identifies the integration site, copy number, integrity, backbone presence and rearrangement of the plasmid insertions by detecting chimeric junction sequences between transformation plasmid and genomic DNA or noncontiguous plasmid DNA. Short sequences generated from transgenic plants are post-processed to remove low quality sequences and sequencing errors and to trim off any adapter sequences. The representative sequences from the top 60% abundant clean sequences are then aligned to the plant genome. Endogenous reads are identified and excluded from downstream junction identification step.

Figure 7A:
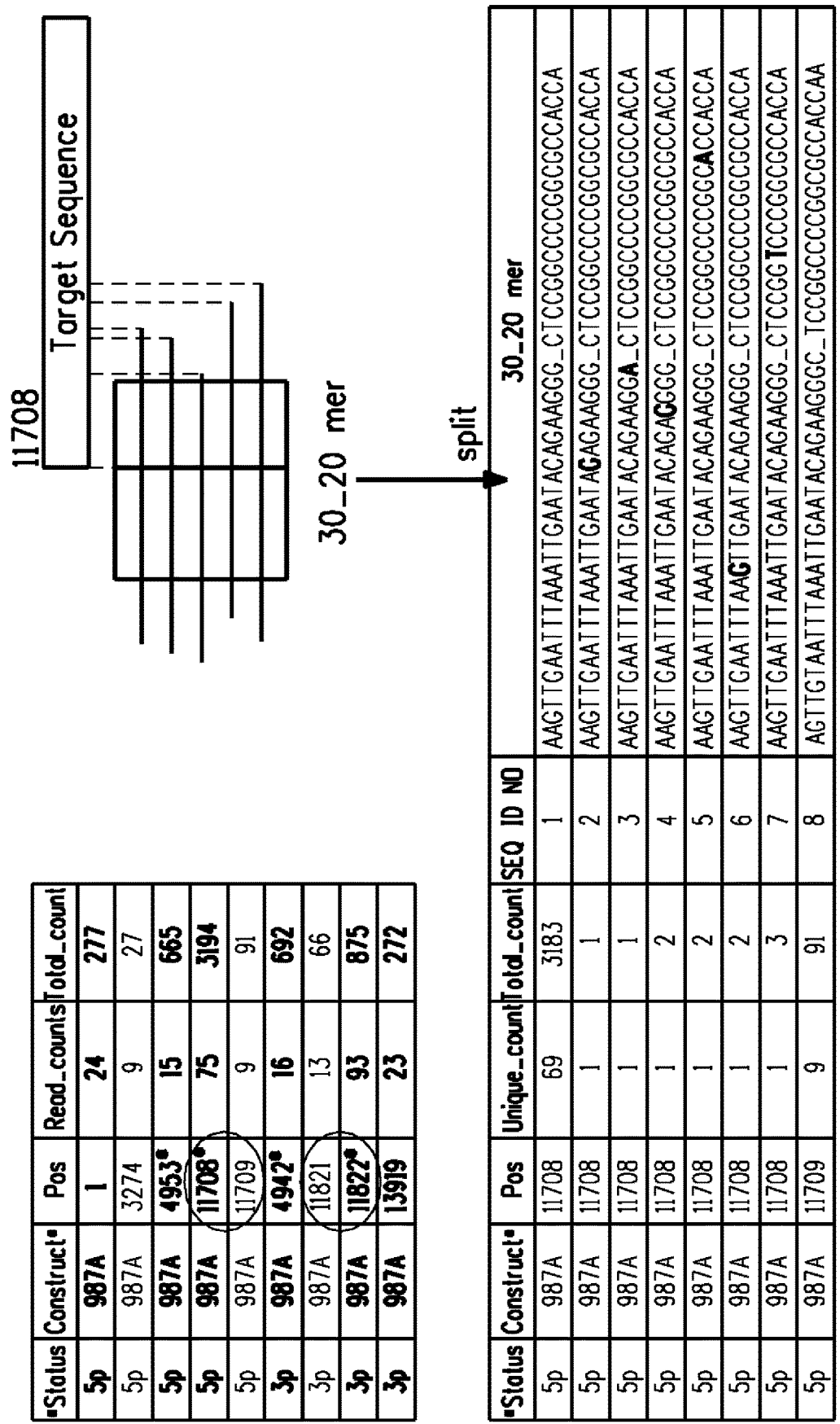

The junctions, either between the plasmid and the plant genomic segment or between noncontiguous plasmid segments are then identified by aligning the remaining non-endogenous reads to the plasmid reference. The junctions are then condensed based on 50 bases of the junction sequence containing 20 bases aligned to the plasmid and 30 noncontiguous bases. The split and condense feature examines junction sequences that are identified as being in the same region. If the junction sequences are identical but for a single nucleotide difference (SNP, insertion, deletion), then the algorithm reports the unique 30_20mer with the most support, i.e., the junctions with low supporting read count are filtered. (see FIGS. 7a and 7b). The junctions that are present in a non-transgenic control from the same or close genotype are also filtered.

For each of the remaining junctions, the tool SSAKE (The Short Sequence Assembly by K-mer search and 3' read Extension) is used to extend the chimeric junction reads into longer contigs using all the clean reads. Each junction can have multiple S SAKE contigs generated. Each SSAKE contig is split at the junction position into one proximal sequence and one distal sequence based on the 30_20 mer, where the proximal sequence refers to the subsequence containing the 20mer of the 30_20 mer while distal sequence refers to the subsequence containing the 30mer of the 30_20 mer. The longest distal sequence of each junction is then mapped to the plant genome to identify the integration site as well as the plasmid to identify any re-arrangement. The longest proximal sequence is mapped to the plasmid to further confirm the junction position of the plasmid. An advancement decision is then made based on a set of criteria based on the analysis result, such as copy number, integrity, backbone absence/presence, and etc.

The SbS pipeline works well for enriched sequences of the plasmid and the flanking sequences generated by sequence capture method. It can also be applied for whole genome shotgun sequencing of the transgenic plant.

SbS is a high-throughput pipeline that is developed to minimize the advancement of poor transformation events which would waste millions of dollars in the downstream product development stages. The resolution of SbS is high enough for regulatory requirements.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for characterizing a target sequence of interest in the genome of an organism, the method comprising:
   a) isolating and purifying a sample of genomic DNA;
   b) fragmenting the genomic DNA into fragments to create a library;
   c) ligating the library fragments to adapter sequences having barcodes;
   d) amplifying the genomic DNA having regions of the target sequence of interest using PCR primers, wherein the PCR primers comprise adapter-specific and construct-specific primers, thereby enriching the library for DNA sequences;
   e) pooling the enriched library in equal molar ratios into sample pools;
   f) sequencing the sample pools to obtain reads;
   g) filtering and aligning the reads to the genomic sequence of a control and to the target sequence of interest;
   h) selecting reads that align to the target sequence of interest;
   i) determining junction sequences from the selected reads; and
   j) using the junction sequences to characterize the integrity of the target sequence of interest in the genome of the sample from the organism.

2. The method of claim 1 wherein the sheared genomic DNA fragments range from about 50 base pairs in length to about 2.5 kb in length.

3. The method of claim 1 wherein the sheared genomic DNA fragments range from about 200 base pairs in length to about 1 kb in length.

4. The method of claim 1 wherein the sheared genomic DNA fragments are about 400 base pairs in length.

5. The method of claim 1 wherein the PCR primers are nested.

6. The method of claim 1 wherein the PCR primers are overlapping.

7. The method of claim 1 wherein the enriched library is analyzed for PCR artifacts.

8. The method of claim 1, wherein the reads obtained in step (g) are processed to remove any adapter sequence information.

9. The method of claim 1, wherein sequencing in step (g) produces at least 1 million reads.

10. The method of claim 1, wherein the reads are 100 bp paired-end reads.

11. The method of claim 1, wherein the top 60% most abundant reads obtained from step (g) are selected for alignment to the genomic sequence of a control and to the target sequence of interest.

12. The method of claim 1, wherein determining the junction sequences in step (j) comprises aligning at least two reads corresponding to a junction sequence and identifying a consensus junction sequence.

13. The method of claim 12, wherein the consensus junction sequence comprises:
   about 30 nucleotides aligning to the genome sequence of the control, and
   about 20 nucleotides aligning to the target sequence of interest.

14. The method of claim 1, wherein the ends of the junction sequence are extended to provide a junction contig of about 100 to about 3000 nucleotides.

15. The method of claim 14, wherein the ends of the junction sequence are extended by aligning overlapping reads at each end of the junction sequence in order to identify the nucleotide sequence flanking each end of the junction sequence.

16. The method of claim 12, wherein the ends of the junction sequence are extended using SSAKE.

17. The method of claim 1, wherein the ends of the junction sequence are aligned to the genomic sequence of a control and to the target sequence of interest.

18. The method of claim 1, wherein step (h) further comprises excluding endogenous reads from further analysis.

19. The method of claim 1, wherein the organism is a plant, the method further comprising selecting a sample plant for advancement based on the number, location, integrity, or any combination thereof, of the target sequence of interest in the genome of the sample plant.

20. The method of claim 19, further comprising using the selected sample plant in a plant breeding program, wherein a use in the breeding program comprises introgressing a gene of interest in the selected sample plant into another plant, crossing the selected sample plant, pedigree breeding with the selected sample plant, using the selected sample plant recurrent selection, using the selected sample plant in mass selection, or mutation breeding with the selected sample plant.

21. The method of claim 1, further comprising characterizing the integrity of the target sequence of interest by analyzing read alignments to the target sequence to identify insertions, deletions, or rearrangements of the target sequence of interest.

22. The method of claim 1, wherein the organism is a plant.

23. The method of claim 22, wherein the organism is a maize plant, a soy plant, a rice plant, a sorghum plant or a wheat plant.

24. The method of claim 1, further comprising characterizing the number, location, or combinations thereof, of the target sequence of interest.

25. The method of claim 22, further comprising characterizing the number, location, or combinations thereof, of the target sequence of interest.

* * * * *